US009999743B2

(12) United States Patent
Pan et al.

(10) Patent No.: US 9,999,743 B2
(45) Date of Patent: Jun. 19, 2018

(54) SOUND-INDUCED SLEEP METHOD AND A SYSTEM THEREFOR

(71) Applicant: AGENCY FOR SCIENCE, TECHNOLOGY AND RESEARCH, Singapore (SG)

(72) Inventors: Yaozhang Pan, Singapore (SG); Juanhong Yu, Singapore (SG); Cuntai Guan, Singapore (SG); Keong Andrew Ng, Singapore (SG); Ti Eu Chan, Singapore (SG); Zhou Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 222 days.

(21) Appl. No.: 14/898,094

(22) PCT Filed: Jun. 11, 2014

(86) PCT No.: PCT/SG2014/000271
§ 371 (c)(1),
(2) Date: Dec. 11, 2015

(87) PCT Pub. No.: WO2014/200433
PCT Pub. Date: Dec. 18, 2014

(65) Prior Publication Data
US 2016/0151602 A1    Jun. 2, 2016

(30) Foreign Application Priority Data
Jun. 11, 2013  (SG) ................................ 201304490-4

(51) Int. Cl.
*A61M 21/02*  (2006.01)
*A61B 5/048*  (2006.01)
(Continued)

(52) U.S. Cl.
CPC ............ *A61M 21/02* (2013.01); *A61B 5/048* (2013.01); *A61B 5/4812* (2013.01); (Continued)

(58) Field of Classification Search
CPC ......................................... A61M 21/00–21/02
See application file for complete search history.

(56) References Cited

U.S. PATENT DOCUMENTS 4,883,067 A    11/1989  Knispel et al.
6,993,380 B1    1/2006  Modarres
(Continued)

FOREIGN PATENT DOCUMENTS

WO    WO 2013/061185 A1    5/2013

OTHER PUBLICATIONS

PCT Notification of Transmittal of the International Search Report and the Written Opinion of the International Searching Authority, or the Declaration for PCT Counterpart Application No. PCT/SG2014/000271, 11 pages, (dated Sep. 12, 2014).
(Continued)

*Primary Examiner* — Thaddeus Cox
(74) *Attorney, Agent, or Firm* — Womble Bond Dickinson (US) LLP (57) ABSTRACT

A method and system for sound-induced sleep is provided. The method includes detecting brainwave signals of a subject. The method further includes analyzing the brainwave signals to determine a current sleepy state of the subject and selecting a sound in response to the current sleepy state based on a quantified association index between the brainwave signals and acoustical features of the sound. The method further more includes playing the sound to the subject.

19 Claims, 7 Drawing Sheets

(51) Int. Cl.
*A61M 21/00* (2006.01)
*A61B 5/00* (2006.01)

(52) U.S. Cl.
CPC .......... *A61B 5/4836* (2013.01); *A61B 5/7275* (2013.01); *A61B 5/7264* (2013.01); *A61M 2021/0027* (2013.01); *A61M 2230/04* (2013.01); *A61M 2230/10* (2013.01)

(56) References Cited

U.S. PATENT DOCUMENTS

| | | |
|---|---|---|
| 7,749,155 B1 | 7/2010 | Anderson et al. |
| 2006/0293608 A1* | 12/2006 | Rothman ............ A61B 5/0476 600/545 |
| 2007/0249952 A1* | 10/2007 | Rubin ................. A61B 5/0476 600/544 |
| 2008/0288023 A1* | 11/2008 | John ................. A61N 1/37247 607/59 |
| 2012/0029378 A1 | 2/2012 | Low |
| 2014/0031712 A1* | 1/2014 | Herskovitz ............ A61B 5/048 600/545 |

OTHER PUBLICATIONS

PCT International Preliminary Report on Patentability (Chapter II of the Patent Cooperation Treaty) for PCT Counterpart Application No. PCT/SG2014/000271, 3 pages, (dated Apr. 22, 2015).

\* cited by examiner

SOUND-INDUCED SLEEP METHOD AND A SYSTEM THEREFOR

CROSS-REFERENCE TO RELATED APPLICATIONS

The present application is a U.S. National Phase Application under 35 U.S.C. § 371 of International Application No. PCT/SG2014/000271, filed 11 Jun. 2014, entitled SOUND-INDUCED SLEEP METHOD AND A SYSTEM THEREFOR, which claims priority to Singapore Patent Application No. 201304490-4, filed 11 Jun. 2013.

FIELD OF THE INVENTION

The present invention generally relates to interactive sleep inducement, and more particularly relates to, a method for sound-induced sleep and a system therefor.

BACKGROUND

The intense life of modern society makes a good quality sleep precious yet difficult. People are too troubled with hectic workloads and family burdens to rest their brains, even when it is time to sleep. To quickly induce good quality sleep, researchers have looked to a number of methods, utilizing an electrocardiogram (ECG) and/or an electroencephalography (EEG) to monitor the sleep quality.

Electrical pulses, for example, transcutaneous electrical nerve stimulator-like pulses (TENS-like pulses), have been used to release endorphins thereby promoting sleep. However, at least one electrode must be contacted with the subject's skin to provide electrical pulses in this method. Also, this method is particular applicable to subjects who are in pain and cannot sleep because of the pain. Yet, a non-invasive and easily implemented method is more desirable, even in regard to patients in pain.

Thus, what is needed is an easy and effective individualizable sleep-inducing method. Furthermore, other desirable features and characteristics will become apparent from the subsequent detailed description and the appended claims, taken in conjunction with the accompanying drawings and this background of the disclosure.

SUMMARY

According to the Detailed Description, a method for sound-induced sleep is provided. The method includes detecting brainwave signals of a subject, analyzing the brainwave signals to determine a current sleepy state of the subject, selecting a sound in response to the current sleepy state based on a quantified association index between the brainwave signals and acoustical features of the sound, and playing the sound to the subject.

In accordance with another aspect, a system for sound-induced sleep is provided. The system includes a detector module, an analyzer module, a processor module and a player module. The detector module is configured to detect brainwave signals of a subject. The analyzer module is configured to analyze the brainwave signals to determine a current sleepy state of the subject. The processor module is configured to select a sound in response to the current sleepy state based on a quantified association index between the brainwave signals and acoustical features of the sound. And the player module is configured to play the sound to the subject.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

Skilled artisans will appreciate that elements in the figures are illustrated for simplicity and clarity and have not necessarily been depicted to scale. For example, the dimensions of some of the elements in the block diagrams or flowcharts may be exaggerated in respect to other elements to help to improve understanding of the present embodiments.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present a novel sound-induced sleep method and a system therefor. The present sound-induced sleep method combines music therapy and brain-computer interface. It continuously and adaptively selects the most suitable sound to quickly induce a good quality sleep. The sound is selected in response to the brainwaves. A system for sound-induced sleep is also proposed to quickly induce a good quality sleep.

Figure 1:
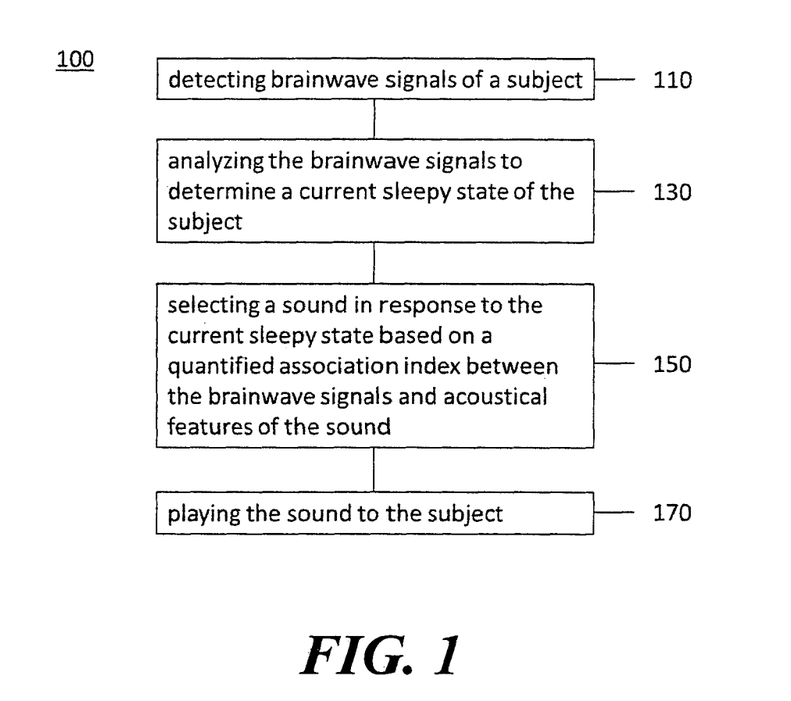
FIG. 1 depicts a flowchart of a method for sound-induced sleep in accordance with a present embodiment.

Referring to FIG. 1, a method 100 for sound-induced sleep in accordance with a present embodiment is depicted. The method 100 comprises detecting brainwave signals of a subject at step 110. While the method 100 and the discussion of the sound-induced sleep in accordance with the present embodiment is limited to detecting brainwave signals of a subject, the present embodiment and the sound-induced sleep method is applicable when other signals are detected from a subject, such as heartbeat signals. The subject discussed herein comprises a human, an animal or any other creature which responds to sound.

The method 100 further comprises analyzing the brainwave signals to determine a current sleepy state of the subject at step 130, selecting a sound in response to the current sleepy state based on a quantified association index between the brainwave signals and acoustical features of the sound at step 150, and playing the sound to the subject at step 170.

Brainwaves are produced by synchronized electrical pulses from masses of neurons communicating with each other in the brain. The brainwave signals are detected using sensors placed on the scalp, such as using sensors for an Electroencephalography (EEG). Brainwaves are divided into bandwidths and each bandwidth is associated with a different sleep state: Delta waves are associated with a deep or dreamless sleep; Theta waves are associated with a light sleep; Alpha, Beta and Gamma waves are associated with awake states. Accordingly, a current sleepy state can be determined from the bandwidth to which the Brainwaves belong. The current sleepy state may comprise a sleepy state and a non-sleepy state. The sleepy state may be associated with Delta waves and Theta waves whereas the non-sleepy state may be associated with Alpha, Beta and Gamma waves. The current sleepy state may also comprise a deep-sleep state, a light-sleep state, a meditation state or a wide-awake state. Each sleepy state may be assigned a sleepiness score to quantify the sleepiness.

The sound played to the subject may comprise music, nature sounds, electronic sounds, and the like. There may be a databank or a sound library for storing such sounds for inducing sleep, such as a sleep therapy compact disk (CD). The selected sound may comprise a single musical song/sound or a list of sounds comprising multiple musical songs and/or other type of sounds. The list of sounds comprised in the selected sound may be pre-stored as a whole in which the sounds are particularly arranged in a preset sequence to induce sleep in accordance with the method as described below.

A sound may be represented and analyzed by its acoustic features. The acoustic features of a sound may comprise a feature selected from the group comprising music signal global energy, tempo, brightness, roughness, Mel-frequency cepstral coefficient, pitch, inharmonicity, key, chromagram, mode, tonal centroid and period entropy. The acoustic features may be computed from ambient music or natural sounds.

The quantified association index between the brainwave signals and the acoustical features of the sound may be obtained by determining a correlation therebetween. The correlation may be expressed using a Canonical Correlation Analysis (CCA). The CCA is a way of measuring the linear relationship between two multidimensional variables by finding the two bases in which the correlation matrix between the variables is diagonal and maximizing the correlations on the diagonal. Accordingly, the CCA simultaneously maximizes the correlation between the brainwave signals and the acoustical features of the sound and maximizes a discrimination between the sleepy state and the non-sleepy state.

The optimization problem using the CCA can be formulated as:

$$\rho = \max_{\omega_x, \omega_y} \frac{\omega_x^T (C_w - C_b) \omega_y^T}{\sqrt{(\omega_x^T C_{xx} \omega_x)(\omega_y^T C_{yy} \omega_y)}} \quad (6)$$

where $$C_w = \sum_{j,k \in same\ class} (x_j y_k^T + x_k y_j^T) \quad (7)$$

represents the correlation of sound-evoked brainwave vector $x_j$ and sound acoustical feature vector $y_j$ from the same class (i.e. both sleepy or non-sleepy), $$C_b = \sum_{j,k \in different\ class} (x_j y_k^T + x_k y_j^T) \quad (8)$$

represents the correlation of $x_j$, $y_j$ from different classes (i.e. one sleepy and the other non-sleepy), $$C_{xx} = XX^T, C_{yy} = YY^T \quad (9)$$

wherein X and Y are matrixes of optimized feature sets obtained from the sound-evoked brainwave signals and the sound acoustical features. $C_{xx}$ and $C_{yy}$ are covariance matrixes representing the correlation among the sound-evoked brainwave signals and the sound acoustical features.

The solution can be obtained using a generalized eigenvalue problem approach, $$(C_w - C_b)(YY^T)^{-1}(C_w - C_b)^T w_x = \lambda^2 XX^T w_x \quad (10)$$

$$(C_w - C_b)(XX^T)^{-1}(C_w - C_b)^T w_y = \lambda^2 YY^T w_y. \quad (11)$$

Eventually, the enhanced brainwave and sound acoustical feature vectors are respectively $$\tilde{X} = W_x^T X, \quad (12)$$

and $$\tilde{Y} = W_x^T Y, \quad (13)$$

where $W_x$ and $W_y$ are eigenvectors corresponding to the largest generalized eigenvalues $\lambda$. $W_x$ and $W_y$ can be viewed as a qualified association index between the brainwave signals and sound acoustical features. Accordingly, a sound acoustical feature will affect the brainwave signal of a subject to whom the sound is played. Therefore, by selecting appropriate sounds based on the qualified association index and playing the sounds, the brainwaves can be manipulated and, thus, a sleep can be induced.

A sleep stage may be determined when analyzing the brainwave signals and the sound may be played accordingly at a predetermined volume determined in response to the sleep stage. The sleep stage may comprise a stage selected from the group comprising wake, light sleep N1, light sleep N2, deep sleep N3 and rapid eye movement sleep (REM). As mentioned above, Delta waves may be associated with the deep sleep N3; Theta waves may be associated with the light sleep N1 and the light sleep N2; and Alpha, Beta and Gamma waves may be associated with the wake stage. The sound may be played at a predetermined starting volume (for example, 100% in the digital domain) in the wake stage, played at a fading volume fading off from a predetermined starting volume and/or discontinued being played in the light sleep stage N1, the light sleep stage N2, the deep sleep stage N3 and the REM sleep stage.

A modelling correspondence between the current sleepy state and the brainwave signals may be preset. The modelling correspondence may be calibrated by manually determining the current sleepy state from an appearance of the subject.

A sleep quality report indicating a total sleeping hour(s), sleep start/end time, and a ratio of light/deep/REM sleep durations may be provided. This is useful for diagnosing any sleep-related diseases.

Figure 2:
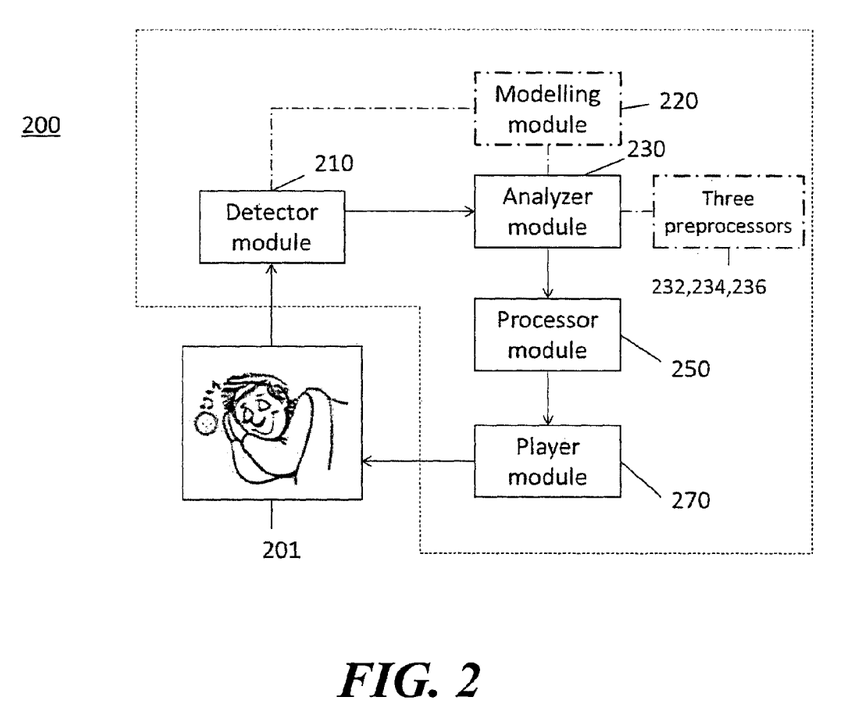
FIG. 2 depicts a block diagram of a system for sound-induced sleep in accordance with the present embodiment.

Referring to FIG. 2, a system 200 for sound-induced sleep is depicted. The system 200 comprises a detector module 210 configured to detect brainwave signals of a subject 201, an analyzer module 230 configured to analyze the brainwave signals to determine a current sleepy state of the subject, a processor module 250 configured to select a sound in response to the current sleepy state based on a quantified association index between the brainwave signals and acoustical features of the sound, and a player module 270 configured to play the sound to the subject.

The analyzer module 230 may be further configured to analyze the brainwave signals in order to determine a sleep stage and the player module 270 is further configured to play the sound at a predetermined volume determined in response to the sleep stage. The sleep stage may comprise a stage selected from the group comprising wake, light sleep (N1), light sleep (N2), deep sleep (N3) and rapid eye movement (REM) sleep.

The player module 270 may further be configured to play the sound at a predetermined starting volume in the wake stage, to play the sound at a fading volume fading off from a predetermined starting volume and/or to discontinuing playing the sound in the light sleep stage N1, the light sleep stage N2, the deep sleep stage and the REM sleep stage.

The processor module 250 may be further configured to provide a sleep quality report indicating a total sleeping hour, sleep start/end time, and a ratio of light/deep/REM sleep durations.

The processor module may be further configured to select the sound in accordance with a preset sequence of sounds.

The system 200 may further comprise a modelling module 220 configured to preset a modelling correspondence between the current sleepy state and the brainwave signals, wherein the modelling correspondence is calibrated by manually determining the current sleepy state from an appearance of the subject.

The system 200 may further comprise three preprocessors (232, 234, and 236) configured from the detected brainwave signals to: 1) detect a noise level; 2) obtain subject-specific baselines; and 3) extract sleep-aware features comprising spindle, K-complex, filter bands (delta, theta, alpha, sigma, beta and gamma). This will be discussed with regards to FIG. 4.

Figure 3:
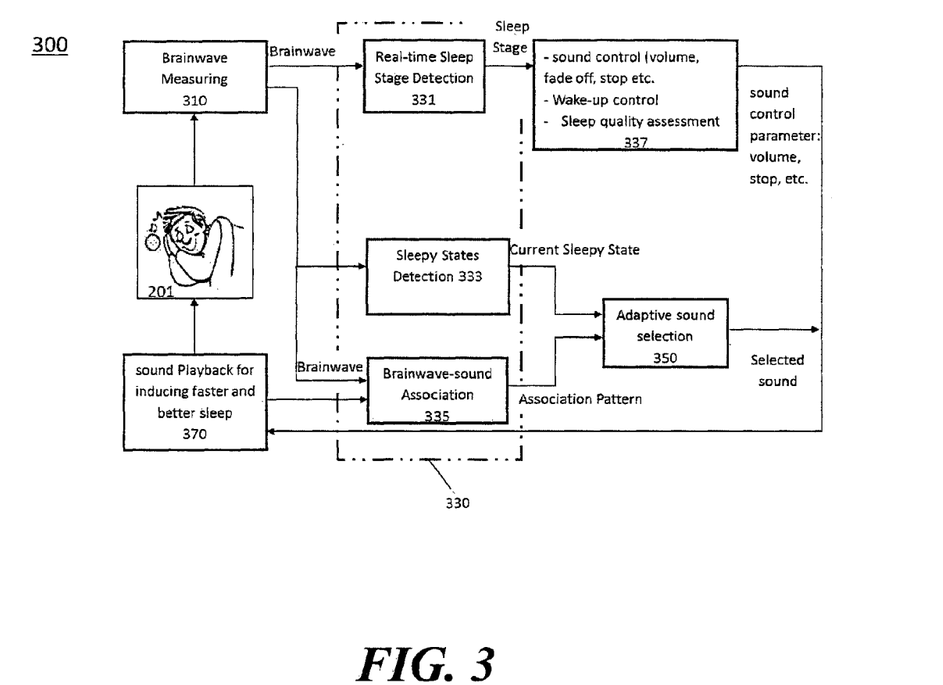
FIG. 3 depicts a flowchart of a method for sound-induced sleep in accordance with the present embodiment.

Referring to FIG. 3, a method for sound-induced sleep is depicted in flowchart 300 in accordance with the present embodiment. Brainwaves of a subject 201 are measured at step 310. The brainwaves are sent to be analyzed at step 330, including a real-time sleep stage detection at step 331, a sleepy states detection at step 333, and a brainwave-sound association at step 335, either simultaneously or serially. Details of the analysis will be discussed in more details with reference to FIG. 4. A sleep stage is determined from the brainwaves during the real-time sleep detection at step 331. A few parameters/actions may be determined in response to the sleep stage at step 337. For example, a sound volume, a wake-up control, or a sleep quality assessment. A current sleepy state is determined after the brainwaves are sent to the sleepy states detection. An association pattern is updated from the pre-stored qualified association index to adapt the subject 301's measured brainwaves. The updated association pattern is sent to adaptive sound selection at step 350. Based on the updated association pattern, sound is adaptively selected in response to the current sleepy state at step 350. In conjunction with the parameters determined at step 337, the selected sound is sent for playing to the subject 301 at step 370. The process is repeatedly going on before and during sleep of the subject 201. Accordingly, the subsequent sound is selected based on the brain response of each individual subject to the previous sound. Thus, the present method provides an individualizable sleep-inducing method by adaptively selecting sounds for each particular individual subject.

Figure 4:
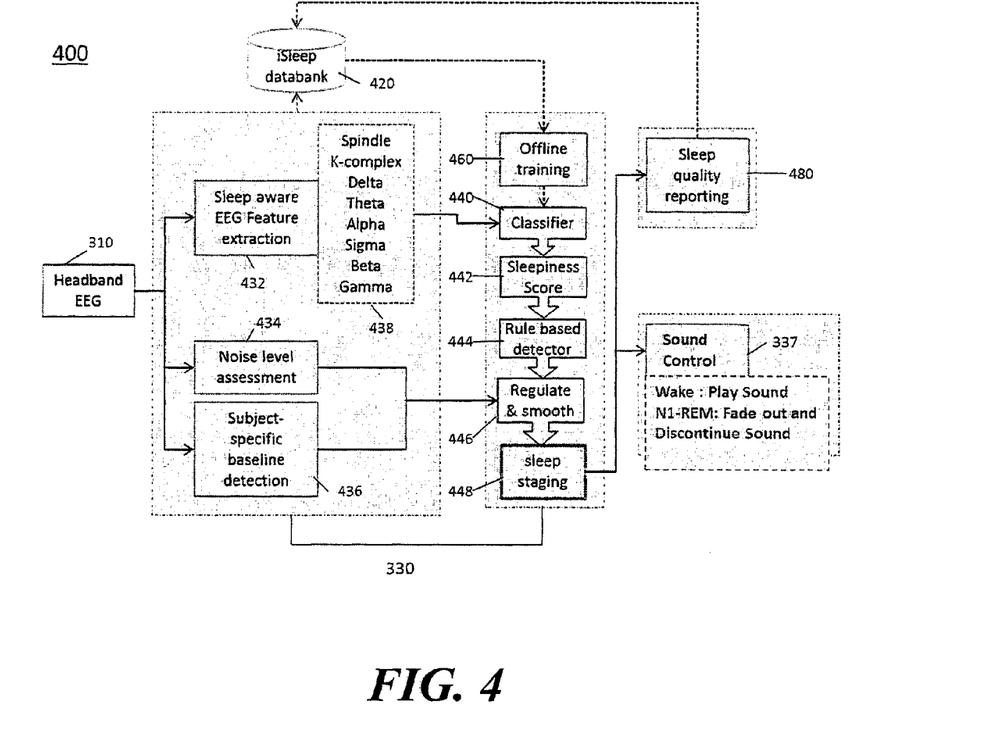
FIG. 4 depicts a flowchart of a method for sound-induced sleep in accordance with the present embodiment.

The analysis of the brainwaves including determination of the sleep stage and sleepy state at step 330 in FIG. 3 is now described in more details with reference to FIG. 4.

The brainwave signals are measured by a headband EEG sensor 310. The brainwave signals are then sent to three preprocessors for three actions: sleep aware EEG feature extraction 432, noise level assessment 434, and subject-specific baseline detection 436. The noise level assessment 434 is used to detect the noise level of the EEG signals. The subject-specific baseline detection 436 is used to obtain a baseline for each subject. The baseline detection may be performed using the first two minutes of EEG signals. Spectral power distribution pattern is acquired and saved as a subject-specific baseline. In this manner, the sleep stage is individually determined and then the sound is individually selected in response to each subject. The results of the noise level assessment and the subject-specific baseline detection are to be used to regulate and smooth the extracted sleep aware EEG feature at a later stage 446.

The sleep aware EEG feature extraction 432 extracts various sleep-aware features from the brainwave signals detected by the EEG, including sleep spindle, K-complex, and filter bands (delta (0.3-4 Hz), theta (4-8 Hz), alpha (8-12 Hz), sigma (12-16 Hz), beta (16-32 Hz), and gamma (32-64 Hz)), as shown at step 438. Furthermore, mean and variations of each filter band power ratio within each epoch are calculated and distribution of each filter band is obtained. The extracted sleep-aware EEG features are fed to a classifier at step 440. The classifier is offline trained by utilizing the data from a databank 420 to discriminate sleepy from non-sleepy state in step 460. The output of the classifier is a continuous parameter, defined as sleepiness score 442. For example, if the sleepiness score is 10 the subject may be in a wake stage (i.e. non-sleepy state) whereas if the sleepiness score is 90 the subject may be in a deep sleep stage. The score is then sent to a fuzzy rule based sleep stage detector 444 to detect the subject's sleep stages, including wake stage, light sleep stage (N1), light sleep stage (N2), deep sleep stage (N3), and REM sleep stage. The EEG noise level and subject-specific EEG baselines are used to regulate the detected sleep stage at step 446. The rule-based decision system is initially trained at step 460 using sleep EEG data labeled, by a sleep specialist and saved in the databank 420. The rule-based decision system will be derived when more EEG data is continuously being collected. A smoothing postprocessor is applied to refine the sleep stages at step 448. A sleep stage is determined by analysing the brainwaves of the subject.

Playback of sound is automatically controlled in terms of volume according to the subject's sleep stages (wake, light sleep, deep sleep stage, and rapid eye movement sleep) at step 337. For instance, sound will be played during wake stage, but gradually faded out and completely discontinued during light sleep stage 1 (non-REM stage N1), during light sleep stage 2 (non-REM stage N2), as well as during deep (non-REM stage N3) and REM sleep stages. As both deep and REM sleep stages are important for replenishing and repairing human body, as well as learning and memory consolidation, sound is not played during these sleep stages to avoid interfering with such activities of the brain. In this manner, the present method induces a quick and good quality sleep.

The whole night's sleep stage data will be consolidated into a sleep quality report at step 480 which summarizes a total sleep hour, sleep start/end time, and the ratio of light/deep/REM sleep durations. The preprocessed data and report will be stored into the databank for future refinement of the sleep detection model.

Figure 5:
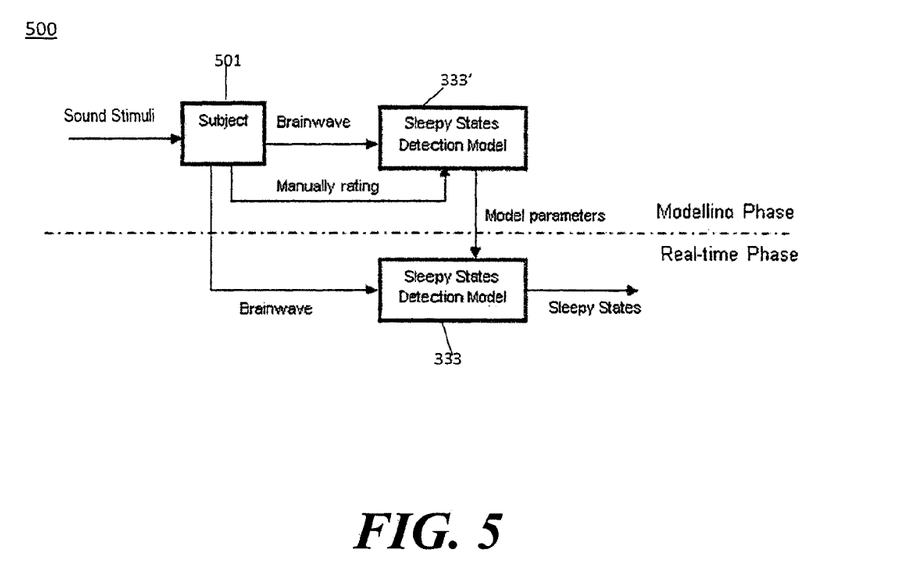
FIG. 5 depicts a flowchart of modelling of the sleepy states detection depicted in FIG. 3 in accordance with the present embodiment.

The sleepy state detection as shown at step 333 in FIG. 3 is now described in more details with reference to FIG. 5. A modelling of brain response between the current sleepy state and the brainwave signals may be performed beforehand to have a preset sleepy state detection model. This can be performed by manually rating sleepiness from the appearance of the subject as well as by recording brainwaves to calibrate the model. For example, visual signs of the light sleep stage N1 may include active muscles, and the eyes rolling slowly with eyelids opening and closing moderately. In the light sleep stage N2, the subject may become gradually harder to awaken. In the deep sleep stage N3, the subject is less responsive to the environment and many environmental stimuli no longer produce any reaction. Visual signs of the REM sleep stage include most muscles being paralyzed; also arousal and oxygen consumption by the brain is higher than when the subject is awake. The calibrated model will capture the brain response of sleepy states (sleepy or non-sleepy) to differentiate sound stimulus.

Referring to FIG. 5, the sound stimuli are received by a subject 501. The brainwaves of the subject 501 are measured in the modelling phase and the sleepy state of the subject 501 is observed manually and rated so that this information is utilized to form a preset sleepy state model at a sleepy states detection model 333'. Thereafter, the model parameters determined at the sleepy states detection model 333' are used during the real-time phase to determine the sleepy states of the subject from is brainwaves at a sleepy states detection model 333 which associates brainwave activity with the predetermined subject sleepy state.

A novel frequency optimization method is adopted to model the brain responses to sound stimulus. The idea is to find the optimal spectral filters to maximize the separation between sleep and non-sleepy states. This way, a sleepy state of a subject is quantified by his brainwave, which is the key leading to the selection of the most suitable sound inducing further sleepy states, together with other modules introduced herein. The modelling process is conducted offline using pre-recorded EEG signal from large quantities of subjects in order to have better generalization performance.

Figure 6:
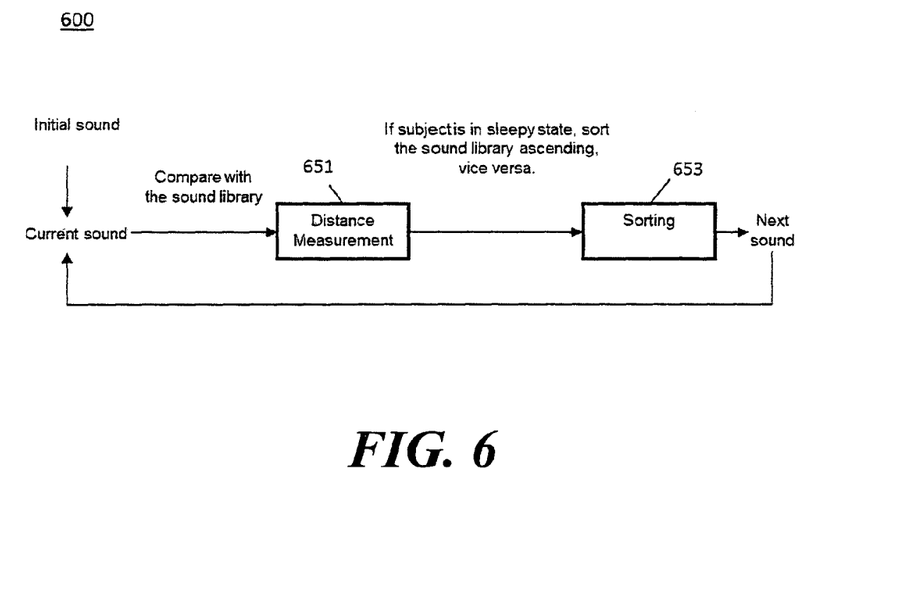
FIG. 6 depicts a flowchart of selecting sound in accordance with the present embodiment.

Referring to FIG. 6, a selecting sound step is depicted. Based on the sleepy state detected and the brain-sound association quantified, the most suitable sound can be automatically and adaptively selected from a sound library to fit the current brain state of the subject. In the sound library, Euclidean distance of sound acoustical feature vectors for each sound is measured at step 651 and a similarity of the sounds is calculated. The sound may be stored in a sequence determined in response to the similarity between the sounds. If the subject's sleepiness is increasing according to the sleepiness score of the subject, the sound will continue playing and a new sound with similar acoustic features to the previous song will be chosen to be subsequently played. On the other hand, if the subject's sleepiness is not increasing according to the sleepiness score of the subject, the sound will discontinue playing and a new sound with least similar acoustic features to the previous song will be chosen to be subsequently played. This selection process is performed at step 653.

Figure 7:
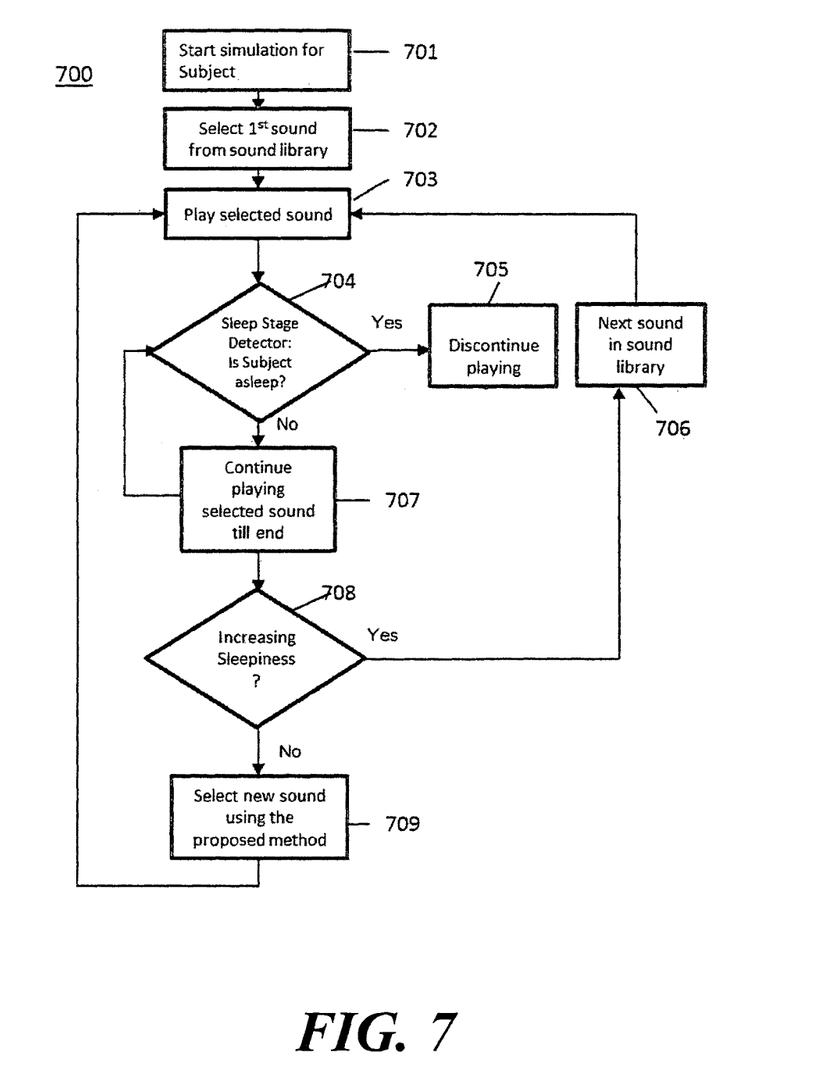
FIG. 7 depicts a flowchart of an evaluation process of a sound-induced sleep method in accordance with the present embodiment.

Referring to FIG. 7, operation of the method for sound-induced sleep is depicted in flowchart 700. This is for an evaluation of the method described herein.

EEG signals were acquired using a headband with a sampling rate of 256 Hz. The EEG signals were collected from twenty-eight healthy subjects. Two EEG electrodes were attached horizontally to the subjects' forehead. The left and right electrodes correspond to FP1 and FP2 respectively. Sound with known acoustical features is stored in a sound library. The sound library includes forty pieces of music from several CD that special designed for sleep therapy.

Before the evaluation process, two sessions of data collection were performed subsequently for each subject. Before starting data collection, the subjects were given some time to calm down and concentrate on the listening to the sound. Each subject was instructed to sit comfortably and minimize body movement when listening to sound. In each session, the subjects continuously listen to the sound and after finish label each piece of sound as sleepy or non-sleepy. For confirmation, the subjects were then asked to tell whether they feel sleepy or not after listening to the sound. These manually rating data will serve as a ground fact for the evaluation.

The evaluation process comprises two parts: one is to select sound according to the present method and the other is to randomly select sound.

Part one is described with reference to FIG. 7. The process is started for subject 1 at step 701. A first sound is randomly selected from the sound library and played to the subject at steps 702 and 703. At step 704, the subject is assessed on whether he/she is asleep. Based on the assessment, the process will go to step 705 if the subject is asleep or go to step 707 if the subject is not asleep. The first sound will discontinue playing at step 705. However, if the subject is awakened after he falls asleep, the process will resume from step 706 again. The first sound continues playing at step 707. During the period of playing the sound, an interval check is performed from step 707 to step 704 to assess the subject on whether he/she is asleep. The check may periodically be performed every three seconds. Following step 707 and at the end of the first sound playing, the subject is again assessed on whether his/her sleepiness is increasing at step 708. Based on the assessment, the process will now go to step 706 if the subject is increasing in sleepiness. A next sound in the sound library will be played at step 706. Alternatively, if the subject is not increasing in sleepiness, the process will go to step 709. A new sound will be selected in accordance with the present method at step 709 and played at step 703. In any event, the process will be repeated from step 703.

In this part one of the evaluation process, the initial first sound is randomly selected from the sounds in the sound library. Then the sleepy states detection module will select the next new sound according to the current sleepy state of the subject. The new sound is selected based on the qualified association index between the brainwaves and the acoustical features of the sounds. This process will continue until the sleep stage detection module finds that the subject has already fallen asleep and decides to discontinue playing sounds.

Part two of the evaluation process is performed similar to part one except that the new sound is randomly selected from the sound library at step 709, instead of selecting the new sound based on the present method.

The effectiveness of sound on each subject in terms of sleep inducement, a sleepy percentage is calculated as below based on the manually rating data collected above:

Sleepy percentage=No. of sound that the subject feel sleepy/Total No. of sound     (14)

To evaluate the present real-time adaptive sound selection, the EEG signal and the collected rating data of the sound are used for reference. In the evaluation process, for each sound selected a precision is calculated as below for part one and part two, respectively. If the rating of the sound selected is 'sleepy' it is treated as a "true positive", and, if the rating is "not sleepy", it is treated as a "false positive".

$$\text{Precision} = \text{No. of true positive/Total No. of sound} \quad (15)$$

The results of the twenty-eight subjects are shown in Table 1. It can be seen that the precision (an average of 47.41) for part two, i.e. random selection of sounds, is close to the sleepy percentage (an average of 47.86) of the sound. However, the precision (an average of 88.11) for part one, i.e. adaptive sound selection based on the proposed method, is much higher than the sleepy percentage. That means the performance of the proposed method based on the current brain states is significantly more effective than the random music selection.

TABLE 1

| Subjects | Sleepy Percentage (manual rating) | Precision (Random selection) | Precision (Brainwave-sound associated selection) |
|---|---|---|---|
| Subject 1 | 57.5 | 62.5 | 83.33 |
| Subject 2 | 30 | 37.5 | 66.67 |
| Subject 3 | 15 | 15 | 100.00 |
| Subject 4 | 27.5 | 32.5 | 100.00 |
| Subject 5 | 7.5 | 12.5 | 100.00 |
| Subject 6 | 62.5 | 57.5 | 95.85 |
| Subject 7 | 25 | 25 | 96.67 |
| Subject 8 | 62.5 | 50 | 96.67 |
| Subject 9 | 45 | 45 | 96.67 |
| Subject 10 | 55 | 50 | 80.00 |
| Subject 11 | 15 | 17.5 | 88.00 |
| Subject 12 | 80 | 75 | 80.33 |
| Subject 13 | 62.5 | 57.5 | 83.33 |
| Subject 14 | 40 | 50 | 83.33 |
| Subject 15 | 90 | 95 | 100.00 |
| Subject 16 | 45 | 45 | 100.00 |
| Subject 17 | 87.5 | 92.5 | 100.00 |
| Subject 18 | 65 | 67.5 | 66.67 |
| Subject 19 | 22.5 | 12.5 | 78.50 |
| Subject 20 | 45 | 32.5 | 100.00 |
| Subject 21 | 50 | 52.5 | 66.67 |
| Subject 22 | 12.5 | 15 | 100.00 |
| Subject 23 | 45 | 42.5 | 83.33 |
| Subject 24 | 77.5 | 67.5 | 66.67 |
| Subject 25 | 37.5 | 40 | 95.00 |
| Subject 26 | 50 | 65 | 92.45 |
| Subject 27 | 75 | 70 | 86.67 |
| Subject 28 | 52.5 | 42.5 | 80.33 |
| Average | 47.86 | 47.41 | 88.11 |

Thus, in accordance with the present embodiment, an easy and effective sleep-inducing method and a system therefor has been presented which overcomes the drawback of the prior art. A method to generate sleepiness score has been presented based on a user's EEG signal. However, the present embodiment can be applied when an ECG signal is monitored. The sleepiness score reflects brain responses to sound stimulus regarding sleepiness. A new innovation of adaptively selecting sound based on the quantified association index between sleepy state and the sound has been proposed for inducing faster and better sleep. A novel strategy of controlling sound playback based on different sleep stages (wake, light sleep, deep sleep, and rapid eye movement sleep) has been presented, which is automatically identified by a real-time sleep stage detector using prefrontal brainwaves (EEG signals).

While exemplary embodiments have been presented in the foregoing detailed description of the invention, it should be appreciated that a vast number of variations exist. For example, those skilled in the art will realize from the teachings herein that the present technology may also be applied when an ECG signal is monitored.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

What is claimed is:

1. A method for sound-induced sleep comprising:
    detecting brainwave signals of a subject;
    analyzing the brainwave signals to determine a current sleepy state of the subject;
    selecting a sound in response to the current sleepy state of the subject based on a quantified association index between the brainwave signals of the subject and acoustical features of the sound, wherein the current sleepy state of the subject comprises a sleepy state of the subject and a non-sleepy state of the subject, and wherein the quantified association index is obtained by determining a correlation between brainwave signals of the subject and the acoustical features of the sound, the correlation being expressed using a Canonical Correlation Analysis which simultaneously maximizes the correlation between the brainwave signals of the subject and the acoustical features of the sound and maximizes a discrimination between the sleepy state of the subject and the non-sleepy state of the subject; and
    playing the sound to the subject.

2. The method of claim 1, wherein analyzing the brainwave signals comprises analyzing the brainwave signals to further determine a sleep stage and playing the sound comprises playing the sound at a predetermined volume determined in response to the sleep stage.

3. The method of claim 2, wherein the sleep stage comprises a stage selected from the group comprising a wake stage, a light sleep stage N1, a light sleep stage N2, a deep sleep stage N3 and a rapid eye movement (REM) sleep stage.

4. The method of claim 3, wherein playing the sound at the predetermined volume determined in response to the sleep stage comprises playing the sound at a predetermined starting volume in the wake stage, playing the sound at a fading volume fading off from a predetermined starting volume and subsequently discontinuing the sound in the light sleep stage N1, the light sleep stage N2, the deep sleep stage and the REM sleep stage.

5. The method of claim 1, further comprising:
    providing a sleep quality report indicating total sleeping hours, sleep start/end times, and a ratio of light/deep/REM sleep stage durations.

6. The method of claim 1, wherein selecting the sound comprises selecting the sound in accordance with a preset sequence of sounds.

7. The method of claim 1, further comprising:
    presetting a modelling correspondence between the current sleepy state and the brainwave signals,
    wherein the modelling correspondence is calibrated by manually determining the current sleepy state from an appearance of the subject.

8. The method of claim 1, wherein the acoustical features comprise a feature selected from the group comprising music signal global energy, tempo, brightness, roughness, Mel-frequency cepstral coefficient, pitch, inharmonicity, key, chromagram, mode, tonal centroid and period entropy.

9. The method of claim 1, wherein the acoustical features are computed from ambient music and natural sounds.

10. A system for sound-induced sleep comprising:
   a detector module configured to detect brainwave signals of a subject;
   an analyzer module configured to analyze the brainwave signals to determine a current sleepy state of the subject, wherein the current sleepy state of the subject comprises a sleepy state of the subject and a non-sleepy state of the subject;
   a processor module configured to select a sound in response to the current sleepy state based on a quantified association index between the brainwave signals and acoustical features of the sound, wherein the processor module obtains the quantified association index by determining a correlation between the brainwave signals and the acoustical features of the sound, the correlation being expressed using a Canonical Correlation Analysis which simultaneously maximizes the correlation between the brainwave signals of the subject and the acoustical features of the sound and maximizes a discrimination between the sleepy state of the subject and the non-sleepy state of the subject; and
   a player module configured to play the sound to the subject.

11. The system of claim 10, wherein the analyzer module is further configured to analyze the brainwave signals to determine a sleep stage and the player module is further configured to play the sound at a predetermined volume determined in response to the sleep stage.

12. The system of claim 11, wherein the sleep stage comprises a stage selected from the group comprising a wake stage, a light sleep stage N1, a light sleep stage N2, a deep sleep stage N3 and a rapid eye movement sleep stage (REM).

13. The system of claim 12, wherein the player module is further configured to play the sound at a predetermined starting volume in the wake stage, play the sound at a fading volume fading off from the predetermined starting volume and subsequently stop playing the sound in the light sleep stage N1, the light sleep stage N2, the deep sleep stage and the REM sleep stage.

14. The system of claim 10, wherein the processor module is further configured to provide a sleep quality report indicating total sleeping hours, sleep start/end times, and a ratio of light/deep/REM sleep stage durations.

15. The system of claim 10, wherein the processor module is further configured to select the sound in accordance with a preset sequence of sound.

16. The system of claim 10, further comprising:
   a modelling module configured to preset a modelling correspondence between the current sleepy state and the brainwave signals,
   wherein the modelling correspondence is calibrated by manually determining the current sleepy state from an appearance of the subject.

17. The system of claim 10, wherein the acoustical features comprise a feature selected from the group comprising music signal global energy, tempo, brightness, roughness, Mel-frequency cepstral coefficient, pitch, inharmonicity, key, chromagram, mode, tonal centroid and period entropy.

18. The system of claim 10, wherein the acoustical features are computed from ambient music and natural sounds.

19. The system of claim 10, further comprising:
   three preprocessors configured to extract from the detected brainwave signals to: detect a noise level, obtain subject-specific baselines, and extract sleep-aware features comprising spindle, K-complex, delta filter band, theta filter band, alpha filter band, sigma filter band, beta filter band and gamma filter band.

* * * * *